United States Patent
Smith et al.

(10) Patent No.: US 10,188,581 B2
(45) Date of Patent: Jan. 29, 2019

(54) METHOD AND SYSTEM TO EVACUATE ONE OR MORE DRESSINGS USING TWO OR MORE VACUUM PUMPS

(71) Applicant: KCI LICENSING, INC., San Antonio, TX (US)

(72) Inventors: Kenneth R. Smith, San Antonio, TX (US); Daniel W. Dekruif, San Antonio, TX (US); Dave E. Ball, San Antonio, TX (US); James A. Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 962 days.

(21) Appl. No.: 14/619,672

(22) Filed: Feb. 11, 2015

(65) Prior Publication Data

US 2015/0231021 A1 Aug. 20, 2015

Related U.S. Application Data

(60) Provisional application No. 61/942,140, filed on Feb. 20, 2014.

(51) Int. Cl.
*A61M 27/00* (2006.01)
*A61F 13/00* (2006.01)
(Continued)

(52) U.S. Cl.
CPC .......... *A61H 9/0057* (2013.01); *A61M 1/0088* (2013.01); *A61M 27/00* (2013.01); *A61F 2013/00536* (2013.01)

(58) Field of Classification Search
CPC ..... A61H 9/0057; A61M 1/00; A61M 1/0088; A61M 27/00; A61F 13/00068;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Timothy Stanis

(57) ABSTRACT

Systems, apparatuses, and methods for providing a negative-pressure therapy system are described. The system includes a first dressing, a second dressing, and a negative-pressure source. The negative-pressure source includes a first pump and a second pump. A first valve is fluidly coupled to the first dressing and the first pump to selectively permit fluid communication to the first dressing. A second valve is fluidly coupled to the second dressing and the second pump to selectively permit fluid communication to the second dressing. A cross-over valve is fluidly coupled to the first pump, the first valve, the second pump, and the second valve. The cross-over valve permits fluid communication between the first pump and the second valve and/or the second pump and the first valve. A controller is communicatively coupled to the first pump, the second pump, the first valve, the second valve, and the cross-over valve for operating the same.

19 Claims, 6 Drawing Sheets

(51) Int. Cl.
*A61H 9/00* (2006.01)
*A61M 1/00* (2006.01)

(58) Field of Classification Search
CPC ...... A61F 2013/0089; A61F 2013/0017; A61F 2013/00174; A61F 2013/0028; A61F 2013/00536
USPC ........... 601/6, 7, 10; 604/304–308, 313, 319
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 9,028,459 B2 * | 5/2015 | Coulthard ......... A61F 13/00055 604/319 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0183702 A1 * | 12/2002 | Henley ............... A61M 1/0001 604/305 |
| 2002/0198504 A1 | 12/2002 | Risk et al. |
| 2006/0079852 A1 | 4/2006 | Bubb et al. |
| 2011/0275964 A1 | 11/2011 | Greener |
| 2013/0144227 A1 | 6/2013 | Locke et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |

(56) References Cited

FOREIGN PATENT DOCUMENTS

| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "a Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for PCT/US2015/015499 dated May 21, 2015.

* cited by examiner

METHOD AND SYSTEM TO EVACUATE ONE OR MORE DRESSINGS USING TWO OR MORE VACUUM PUMPS

CROSS-REFERENCE TO RELATED APPLICATIONS

This application claims priority to and the benefit of U.S. Provisional Patent Application No. 61/942,140, filed Feb. 20, 2014, entitled "METHOD AND SYSTEM TO EVACUATE ONE OR MORE DRESSINGS USING TWO OR MORE VACUUM PUMPS," to Kenneth R. Smith, Daniel W. DeKruif, Dave Ball, and James Luckemeyer, which is hereby incorporated by reference.

TECHNICAL FIELD

The invention set forth in the appended claims relates generally to tissue treatment systems and more particularly, but without limitation, to a multi-pump negative-pressure therapy system.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for a multi-pump negative-pressure therapy system in a negative-pressure therapy environment are set forth in the appended claims. Illustrative embodiments are also provided to enable a person skilled in the art to make and use the claimed subject matter. For example, a system is described herein that may include a first dressing adapted to be positioned adjacent a first tissue site, and a second dressing adapted to be positioned adjacent a second tissue site. The system may include a negative-pressure source. The negative-pressure source may include a first pump having an outlet and adapted to be fluidly coupled to the first dressing, and a second pump having an outlet and adapted to be fluidly coupled to the second dressing. The negative-pressure source may include a first valve having an outlet fluidly coupled to the first dressing and an inlet fluidly coupled to the outlet of the first pump and adapted to selectively permit fluid communication to the first dressing. The negative-pressure source also may include a second valve having an outlet fluidly coupled to the second dressing and an inlet fluidly coupled to the outlet of the second pump and adapted to selectively permit fluid communication to the second dressing. The negative-pressure source may further include a cross-over valve having a first port fluidly coupled to an outlet of the first pump and an inlet of the first valve and a second port fluidly coupled to the outlet of the second pump and the inlet of the second valve, the cross-over valve may be adapted to selectively permit fluid communication between the outlet of the first pump and the inlet of the second valve and/or the outlet of the second pump and the inlet of the first valve. The system may further include a controller communicatively coupled to the first pump, the second pump, the first valve, the second valve, and the cross-over valve for selectively operating the first pump, the second pump, the first valve, the second valve, and the cross-over valve.

In another embodiment, a method for providing negative pressure to two or more tissue sites is described. A first dressing may be positioned adjacent a first tissue site, and a second dressing may be positioned adjacent a second tissue site. A negative-pressure source may be fluidly coupled to the first dressing and the second dressing, the negative-pressure source having a first pump, a second pump, and a controller communicatively coupled to the first pump and the second pump for operation of the first pump and the second pump. The negative-pressure source may be operated to provide negative pressure to the first tissue site and the second tissue site. The negative-pressure source may determine if there is a negative-pressure demand and if there is no negative-pressure demand, the negative-pressure source may stop. If there is a negative-pressure demand, the negative-pressure source may determine if there is a low negative-pressure demand. If there is a low negative-pressure demand, the negative-pressure source may operate each pump of the two or more pumps to independently provide negative pressure to a respective dressing. If there is a high negative-pressure demand, the negative-pressure source may operate each pump of the two or more pumps to provide negative pressure to each dressing consecutively.

Alternatively, other example embodiments may provide a negative-pressure source. The negative-pressure source may include a first pump and a second pump. The negative-pressure source may also include a first valve having an inlet fluidly coupled to an outlet of the first pump and a second valve having an inlet fluidly coupled to an outlet of the second pump. The negative-pressure source may further include a cross-over valve having a first port fluidly coupled the outlet of the first pump and the inlet of the first valve, and a second port fluidly coupled to the outlet of the second pump and the inlet of the second valve. A controller may be communicatively coupled to the first pump, the second pump, the first valve, the second valve, and the cross-over valve for operation of the first pump, the second pump, the first valve, the second valve, and the cross-over valve.

In another exemplary embodiment, a method for providing negative pressure to two or more tissue sites may be described. A first dressing may be positioned adjacent a first tissue site, and a second dressing may be positioned adjacent a second tissue site. A negative-pressure source may be fluidly coupled to the first dressing and the second dressing. The negative-pressure source may have a first pump, a second pump, and a controller communicatively coupled to the first pump and the second pump for operation of the first pump and the second pump. The first pump may have a greater capacity than the second pump. The negative-pressure source may be operated to provide negative-pressure therapy as follows. The negative-pressure source may determine a required flow rate. If the required flow rate is not greater than zero, the negative-pressure source may stop. If the required flow rate is greater than zero, the negative-pressure source may determine if the required flow rate is greater than a capacity of the second pump. If the required flow rate is not greater than the capacity of the second pump, the negative-pressure source may provide negative pressure to the first tissue site and the second tissue site with the second pump. If the required flow rate is greater than the capacity of the second pump, the negative-pressure source may determine if the required flow rate is greater than a capacity of the first pump. If the required flow rate is not greater than the capacity of the first pump, the negative-pressure source may provide negative pressure to the first tissue site and the second tissue site with the first pump. If the required flow rate is greater than the capacity of the first pump, the negative-pressure source may provide negative pressure to the first tissue site and the second tissue site with both the first pump and the second pump.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
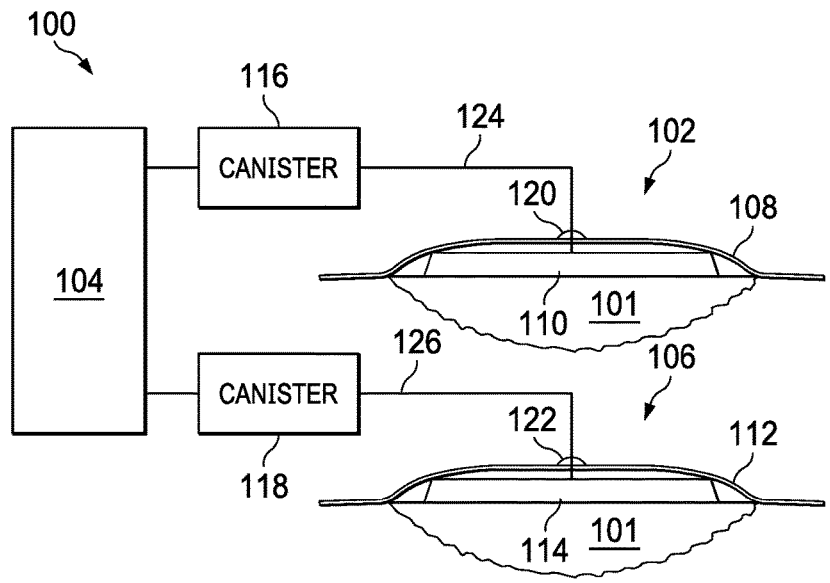
FIG. 1 is a functional block diagram of an example embodiment of a negative-pressure therapy system that can provide negative pressure to two or more tissue sites in accordance with this specification.

FIG. 1 is a simplified functional block diagram of an example embodiment of a negative-pressure therapy system 100 that can provide negative-pressure therapy to one or more tissue sites 101. The negative-pressure therapy system 100 may include one or more dressings and a negative-pressure source. For example, a first dressing, such as a dressing 102, may be fluidly coupled to a negative-pressure source 104. A second dressing, such as a dressing 106, may also be fluidly coupled to the negative-pressure source 104. A dressing generally includes a cover and a tissue interface. The dressing 102, for example, includes a cover 108, and a tissue interface 110. The dressing 106, for example, includes a cover 112, and a tissue interface 114. The negative-pressure therapy system 100 may also include one or more fluid canisters, such as a canister 116 and a canister 118. In some embodiments, the canister 116 may be fluidly coupled between the dressing 102 and the negative-pressure source 104 by a connector 120 and a tube 124, and the canister 118 may be fluidly coupled between the dressing 106 and the negative-pressure source 104 by a connector 122 and a tube 126.

In general, components of the negative-pressure therapy system 100 may be coupled directly or indirectly. For example, the negative-pressure source 104 may be directly coupled to the canister 116 and the canister 118 and indirectly coupled to the dressing 102 and the dressing 106 through the canister 116 and the canister 118, respectively. Components may be fluidly coupled to each other to provide a path for transferring fluids (such as liquid, gas, or liquid and gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts. For example, connectors 120 and 122 may be fluidly coupled to tubes 124 and 126, respectively, to provide negative pressure to the dressing 102 and the dressing 106, from the negative-pressure source 104. The negative pressure developed by a negative-pressure source may be delivered through a tube to a connector, such as the connector 120 and the connector 122. In one illustrative embodiment, a connector may be a T.R.A.C.® Pad or Sensa T.R.A.C.® Pad available from KCI of San Antonio, Tex. A connector may allow the negative pressure to be delivered to a dressing. In other exemplary embodiments, a tube may be inserted through the cover 108 or the cover 112.

In operation, the tissue interface 110 and the tissue interface 114 may be placed within, over, on, or otherwise proximate to a respective tissue site. The cover 108 and the cover 112 may be placed over the tissue interface 110 and the tissue interface 114, respectively, and sealed to tissue near the respective tissue sites 101. For example, the cover 108 and the cover 112 may be sealed to peritissue adjacent the tissue sites 101. Thus, the dressing 102 and the dressing 106 can each provide a sealed therapeutic environment proximate to a respective tissue site that is substantially isolated from the external environment. The negative-pressure source 104 can reduce the pressure in each sealed therapeutic environment provided by the dressing 102 and the dressing 106. Negative pressure applied across the tissue site through the tissue interface 110 and the tissue interface 114 in the respective sealed therapeutic environments can induce macrostrain and microstrain in each respective tissue site, as well as remove exudates and other fluids from the tissue site, which can be collected in the canister 116 and the canister 118, respectively, and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102 or the dressing 106. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or pumps that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa). The therapeutic pressure at which negative-pressure therapy is performed may also be referred to as a therapy pressure. In some embodiments, the therapy pressure may be about −125 mm Hg.

The tissue interface 110 and the tissue interface 114 may be adapted to contact a tissue site directly or indirectly, and may be partially or fully in contact with a tissue site. If a tissue site is a wound, for example, the tissue interface 110 and the tissue interface 114 may partially or completely fill the wound, or may be placed over the wound. The tissue interface 110 and the tissue interface 114 may take a variety of forms including, for example, different sizes, shapes, or thicknesses depending on a variety of factors, such as the type of treatment being implemented or the nature and size of a tissue site. For example, the size and shape of the tissue interface 110 and the tissue interface 114 may be adapted to the contours of deep and irregular shaped tissue sites. The tissue interface 110 and the tissue interface 114 may also be different sizes and adapted to the contours of their respective tissue sites.

In some embodiments, the tissue interface 110 and the tissue interface 114 may be a manifold. A "manifold" in this context generally includes any substance or structure that provides a plurality of pathways adapted to collect or distribute fluid across a tissue site under negative pressure. For example, a manifold may be adapted to receive negative pressure from a negative-pressure source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an embodiment of the tissue interface 110 and the tissue interface 114 comprises a hydrophilic material and may also wick fluid away from a tissue site, while continuing to distribute negative pressure to the tissue site. The wicking properties of the tissue interface 110 and the tissue interface 114 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 and the tissue interface 114 may further promote granulation at a tissue site when pressure within the sealed therapeutic environment is reduced. For example, any or all of the surfaces of the tissue interface 110 and the tissue interface 114 may have an uneven, coarse, or jagged profile that can induce microstrains and stresses at a tissue site if negative pressure is applied through the tissue interface 110 or the tissue interface 114.

In some embodiments, the tissue interface 110 and the tissue interface 114 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 and the tissue interface 114 may further serve as a scaffold for new cell-growth, or a scaffold material may be used in conjunction with the tissue interface 110 and the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 and the cover 112 may provide a bacterial barrier and protection from physical trauma. The cover 108 and the cover 112 may also be constructed from a material that reduces evaporative losses and provide a fluid seal between two components or two environments, such as between a therapeutic environment and a local external environment. The cover 108 and the cover 112 may be, for example, an elastomeric film or membrane that can provide a seal adequate to maintain a negative pressure at a tissue site for a given negative-pressure source. In some example embodiments, the cover 108 and the cover 112 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the cover 108 and the cover 112 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 and the cover 112 may be coated with an acrylic adhesive having a coating weight between about 25 grams per square meter (gsm) and about 65 gsm. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The canister 116 and the canister 118 are representative of a container, canister, pouch, or other storage component, which can be used to manage exudates and other fluids withdrawn from a tissue site. In many environments, a rigid canister may be preferred or required for collecting, storing, and disposing of fluids. In other environments, fluids may be properly disposed of without rigid canister storage, and a re-usable canister could reduce waste and costs associated with negative-pressure therapy.

Generally, a negative-pressure source may have a single pump that is used to provide negative-pressure therapy. However, a negative-pressure source having a single pump may suffer some drawbacks when used to provide negative-pressure therapy to more than one tissue site. For example, a negative-pressure therapy system having a single pump may take an extended amount of time to draw down multiple dressings or to draw down a dressing positioned over a large tissue site. "Draw down" or "drawing down a dressing" may refer to the process of providing negative pressure to a tissue site covered by a dressing until the pressure at the dressing drops from atmospheric pressure to the therapy pressure, e.g., −75 mm Hg. During the draw down process, a caregiver may be required to remain near the patient. If draw down takes an extended time period, the time the clinician must spend visually monitoring the patient increases, which may also increase the staffing requirements of a clinic providing negative-pressure therapy. Many negative-pressure sources use a battery to provide the electricity needed to operate a pump. An extended draw down period may cause the use of additional electric power, which can significantly decrease the life of the battery. Moreover, a negative-pressure therapy system having only one pump will no longer be able to provide negative-pressure therapy if the single pump fails.

Some negative-pressure therapy systems attempt to overcome the problems of having a single pump by using a single pump that has a greater pumping capacity than the standard pumps used in negative-pressure sources. However, negative-pressure therapy systems that use a single larger pump may also suffer from other drawbacks. For example, a single large pump may draw down a dressing too fast, which may cause discomfort to the patient. A single large pump may also be significantly louder than a standard pump used in a negative-pressure source. The increased noise of the larger pump may cause irritation to the patient, decreasing the likelihood that negative-pressure therapy may be used. A single larger pump may also require more electric power to operate; consequently, negative-pressure sources having a single larger pump may still suffer from short battery life, or require that the negative-pressure source be connected to an electrical outlet. Negative-pressure sources having a single larger pump may also be inoperable if the single larger pump fails.

Some negative-pressure therapy systems may use a Y-connector to fluidly couple a negative-pressure source to more than one tissue site. Using a Y-connector to fluidly coupled more than one tissue site to the same negative-pressure source may increase the risk of cross-contamination. Cross-contamination may occur if fluid from an infected tissue site interacts with a non-infected tissue site. The fluid from the infected tissue site may cause the infection to spread to the non-infected tissue site. Fluidly coupling more than one tissue site into the same therapy channel with a Y-connector may increase this risk.

These limitations may be overcome by providing a negative-pressure source having two or more pumps. For example, the negative-pressure therapy system 100 can be modified to include two or more pumps to simultaneously evacuate a single dressing. For example, each pump may be fluidly coupled to a single dressing so that both pumps provide negative pressure to the same dressing. In some embodiments, the negative-pressure therapy system can operate the two or more pumps independently to provide multi-channel functionality. For example, each pump may be fluidly coupled to a separate dressing so that each pump provides negative pressure to a different dressing. In some embodiments, the negative-pressure therapy system can use the two or more pumps to provide redundancy to each other. In other embodiments, the negative-pressure therapy system can provide pump optimization to reduce power consumption by staging the two or more pumps to efficiently use a power source. In still other embodiments, the negative-pressure therapy system may provide a negative-pressure source having a weight that is lower than comparable systems. For example, multiple smaller pumps may be used and a smaller battery may be used to provide power to the pumps, reducing the overall weight of a negative-pressure source. In yet other embodiments, the negative-pressure therapy system may produce less sound when operating or have more infrequent periods of excessive noise during operation.

Figure 2:
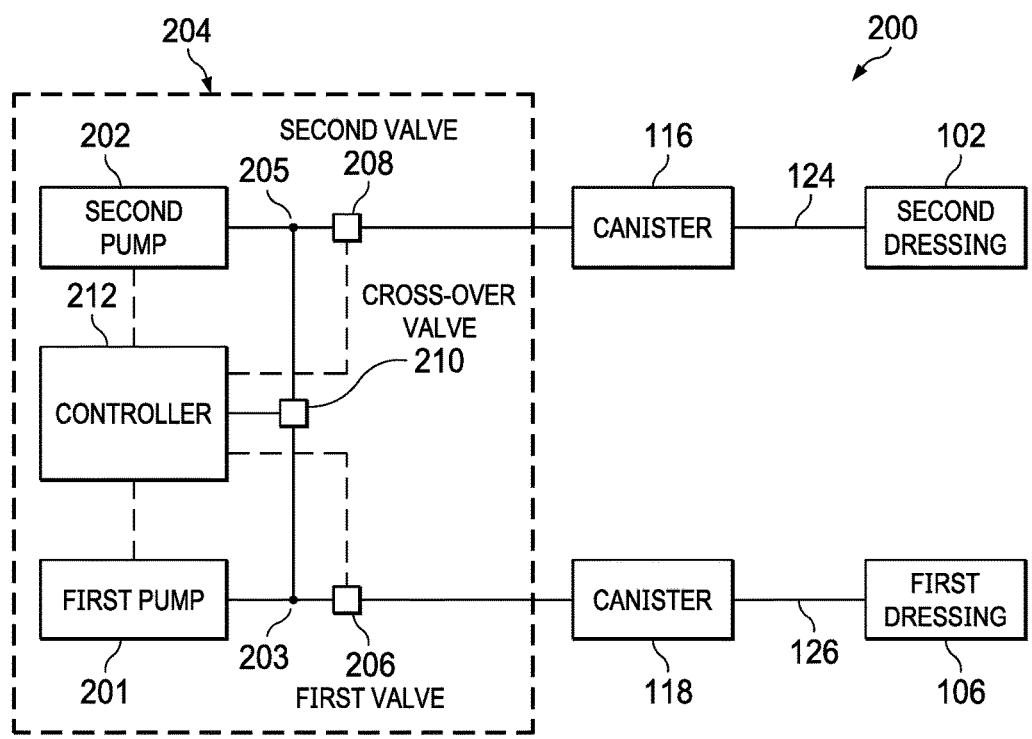
FIG. 2 is a schematic diagram illustrating additional details that may be associated with an example embodiment of the negative-pressure therapy system of FIG. 1.

Referring more specifically to FIG. 2, a modified embodiment of the negative-pressure therapy system 100 is shown as negative-pressure therapy system 200, comprising a negative-pressure source 204 that may include two or more pumps. In some embodiments, the negative-pressure source 204 may include a first pump 201 and a second pump 202. The negative-pressure source 204 may also include a first valve 206, a second valve 208, and a cross-over valve 210. The first valve 206 may be fluidly coupled between the first pump 201 and the canister 118. The second valve 208 may be fluidly coupled between the second pump 202 and the canister 116. The cross-over valve 210 may fluidly couple the first pump 201 and the second pump 202. In some embodiments, the cross-over valve 210 may have a first port fluidly coupled to the first pump 201 by a tee-fitting 203 between the first pump 201 and the first valve 206. Similarly, the cross-over valve 210 may have a second port fluidly coupled to the second pump 202 by a tee-fitting 205 between the second pump 202 and the second valve 208. The negative-pressure source 204 may also include a controller 212. The controller 212 may be communicatively coupled to the first pump 201, the first valve 206, the second pump 202, the second valve 208, and the cross-over valve 210.

A "pump," such as the first pump 201 and the second pump 202, may be a diaphragm pump driven by an electric motor. A diaphragm pump may be a positive displacement pump formed from a chamber having a reciprocating diaphragm. The chamber may have an inlet and an outlet, each having a valve operable to permit flow in one direction. The reciprocating diaphragm may form a portion of the chamber. The reciprocating action of the diaphragm may cause the volume of the chamber to change, drawing fluid into the chamber if the volume is increased and forcing fluid out of the chamber if the volume is decreased. In other embodiments, the first pump 201 and the second pump 202 may be other pump types operable to generate negative pressures as described herein.

In some embodiments, a pump may have a free-air-flow capacity of about 7 liters per minute (lpm) to about 9 lpm. Free-air-flow capacity may refer to the volume of air that may be moved by a pump when the pump is operated in a free space without a load. In some embodiments, a pump may be configured to operate at about 2 lpm. In some embodiments, a Parker Hannifin Corporation BTC-IIS Diaphragm Pump may be used. In some embodiments, a Thomas Products Division, Manufacturer Part No. 14210001 type diaphragm pump may be used. In other embodiments, a pump may have a free-air-flow capacity of about 0.7 lpm, such as Thomas Products Division, Manufacturer Part No. 20020433. In other embodiments, a pump may have a free-air-flow capacity of about 0.3 to about 0.5 lpm, such as Koge KPV08-03A.

Generally, a "valve," such as the first valve 206, the second valve 208, and the cross-over valve 210, may be a device configured to selectively permit fluid flow through the device. A valve may be a ball valve, a gate valve, a butterfly valve, or other valve type that may be operated to control fluid flow through the valve. Generally, a valve may include a valve body having a flow passage, a valve member disposed in the flow passage and operable to selectively block the flow passage, and an actuator configured to operate the valve member. The flow passage may have an inlet and an outlet. An actuator may be configured to position the valve member in a closed position, preventing fluid flow through the flow passage of the valve; an open position, permitting fluid flow through the fluid passage of the valve; or a metering position, permitting fluid flow through the flow passage of the valve at a selected flow rate. In some embodiments, the actuator may be a mechanical actuator configured to be operated by an operator. In some embodiments, the actuator may be an electromechanical actuator configured to be operated in response to the receipt of a signal input, such as a solenoid valve. For example, the actuator may include an electrical motor configured to receive a signal from a controller. In response to the signal, the electrical motor of the actuator may move the valve member of the valve. In some embodiments, the actuator may be a pneumatically operated actuator configured to be operated in response to receipt of a pneumatic input. In some embodiments, a pneumatic input may be negative pressure or positive pressure provided by a pump, such as the first pump 201 or the second pump 202.

A flow capacity for a valve may be selected to minimize pressure drops across the valve while providing a desired flow rate. In some embodiments, a valve may be selected to provide about 2 lpm flow through the valve. In some embodiments, a valve may be a pinch valve. A pinch valve may be a portion of a tube having a clamping device positioned to selectively compress the tube to block passage of fluid through the tube. In some embodiments, the portion of a tube may be a tube formed of an elastomer. In some embodiments, the portion of a tube may be a tube formed of a silicone.

In some embodiments, the first valve 206 may be actuated to selectively permit fluid communication between the first pump 201 and the canister 118. In some embodiments, the second valve 208 may be actuated to selectively permit fluid communication between the second pump 202 and the canister 116. In some embodiments, the cross-over valve 210 may be actuated to selectively permit fluid communication between the first pump 201 and the canister 116 or the second pump 202 and the canister 118.

A "controller," such as the controller 212, may be communicatively coupled to components of a negative-pressure source, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling between a controller and other devices may be one-way communication. In one-way communications, signals may be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in two directions. For example, a controller and a pump may be communicatively coupled so that the controller may send and receive signals from the pump. Similarly, a pump may send and receive signals from a controller. In some embodiments, signal transmission between a controller and another device may be referred to as the controller operating the device. For example, interaction between a controller and a valve may be referred to as the controller: actuating the valve; placing the valve in an open position, a closed position, or a metering position; and opening the valve, closing the valve, or metering the valve.

A controller may be a computing device or system, such as a programmable logic controller, or a data processing system, for example. In some embodiments, a controller may be configured to receive input from one or more devices, such as a pump, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

A controller may be communicatively coupled to one or more sensors positioned in a negative-pressure therapy system. In some embodiments, a controller may be communicatively coupled to a pressure sensor. A pressure sensor may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure. One or more pressure sensors may be positioned throughout the negative-pressure therapy system 200 to provide pressure feedback to the controller 212.

In some embodiments, a controller may be communicatively coupled to a flow meter. A flow meter may be a device configured to determine a fluid flow rate. A flow meter may include a mechanical flow meter, a pressure based flow meter, an optical flow meter, an open channel flow meter, a thermal mass flow meter, a vortex flow meter, electromagnetic, ultrasonic and coriolis flow meters, and laser doppler flow meters. A flow meter may determine a rate of fluid flow through a valve or tube and transmit a signal to a controller, such as the controller 212 corresponding to the determined flow rate. A controller may receive the determined flow rate and determine a total volume of fluid delivered in response. In some embodiments, a flow meter may be a tachometer operatively coupled to a pump motor. The tachometer may be calibrated to provide an estimated flow rate based on pump characteristics in response to a pump speed. In other embodiments, a flow rate may be determined in response to the characteristics of the pump and the operation of the pump that may be needed to maintain the therapy pressure at a tissue site.

In some embodiments, the negative-pressure system 100 may be operated to provide negative pressure to one or both of the dressing 102 and the dressing 106. In some embodiments, the controller 212 may open the first valve 206 and the second valve 208. The controller 212 may also operate the first pump 201 and the second pump 202. If the controller 212 opens the first valve 206 and the second valve 208 and closes the cross-over valve 210, operation of the first pump 201 may generate a negative pressure in the dressing 106. If the controller 212 opens the first valve 206 and the second valve 208 and closes the cross-over valve 210, operation of the second pump 202 may generate a negative pressure in the dressing 102.

In some embodiments, the controller 212 may open the first valve 206 and the cross-over valve 210 and close the second valve 208. If the controller 212 operates the first pump 201, the first pump 201 may generate a negative pressure in the dressing 106. Similarly, if the controller 212 operates the second pump 202, the second pump 202 may generate a negative pressure in the dressing 106. If the controller operates both the first pump 201 and the second pump 202, the first pump 201 and the second pump 202 may both generate a negative pressure in the dressing 106.

In some embodiments, the controller 212 may open the second valve 208 and the cross-over valve 210 and close the first valve 206. If the controller 212 operates the first pump 201, the first pump 201 may generate a negative pressure in the dressing 102. Similarly, if the controller 212 operates the second pump 202, the second pump 202 may generate a negative pressure in the dressing 102. If the controller operates both the first pump 201 and the second pump 202, the first pump 201 and the second pump 202 may both generate a negative pressure in the dressing 102.

In some embodiments, the controller 212 may operate the first valve 206, the second valve 208, and the cross-over valve 210 in response to conditions at one or more of the dressing 102, the dressing 106, the canister 116, and the canister 118. For example, if high negative-pressure demand is needed in one of the dressing 102 or the dressing 106, the cross-over valve 210 and one of the first valve 206 and the second valve 208 can be opened to allow both pumps to run simultaneously to evacuate the dressing 102 or the dressing 106 more quickly than if each pump was used individually. In another example, if there is a low negative-pressure demand, the cross-over valve 210 may be closed and the first valve 206 and the second valve 208 may be opened so that the first pump 201 and the second pump 202 each only provide negative pressure to one of the dressing 102 and the dressing 106. In another example, one of the first pump 201 or the second pump 202 may be used to alternatingly provide negative-pressure to the dressing 102 and the dressing 106. For example, if the dressing 102 and the dressing 106 have a low negative-pressure demand, the cross-over valve 210 may be closed, the first valve 206 may be opened, and the first pump 201 may be operated to provide negative pressure to the dressing 106. If the dressing 106 reaches the therapy pressure, the first valve 206 may be closed, the cross-over valve 210 may be opened, and the second valve 208 may be opened. The first pump 201 may be operated to provide negative pressure to the dressing 102. In this manner, the first pump 201 may be operated to provide negative pressure to the dressing 102 and the dressing 106 using different fluid paths.

In some embodiments, the first pump 201 and the second pump 202 may have different pumping capacities. For example, the first pump 201 may have a free-air-flow capacity between about 7 lpm and about 9 lpm, and the second pump 202 may have a free-air-flow capacity between about 0.3 lpm and about 0.7 lpm. During operation of the negative-pressure therapy system 200, the first pump 201 may be used to draw down both the dressing 102 and the dressing 106. Once the dressing 102 and the dressing 106 have been drawn down, the first pump 201 may be shut off, and the second pump 202 may be used to maintain the therapy pressure at the dressing 102 and the dressing 106. For example, at the start of negative-pressure therapy, the controller 212 may open the first valve 206, the second valve 208, and the cross-over valve 210. The controller 212 may then operate the first pump 201 at a higher flow rate, for example, 4 lpm, to draw down the dressing 102 and dressing 106. Once the dressing 102 and the dressing 106 have reached the therapy pressure, the controller 212 may close the first valve 206, the second valve 208, and the cross-over valve 210. If additional negative pressure is needed at one of the dressings, for example, the dressing 106, the controller 212 may open the first valve 206 and the cross-over valve 210. The controller 212 may operate the second pump 202 to provide additional negative pressure at a lower flow rate, for example 0.5 lpm, to the dressing 106.

Figure 3:
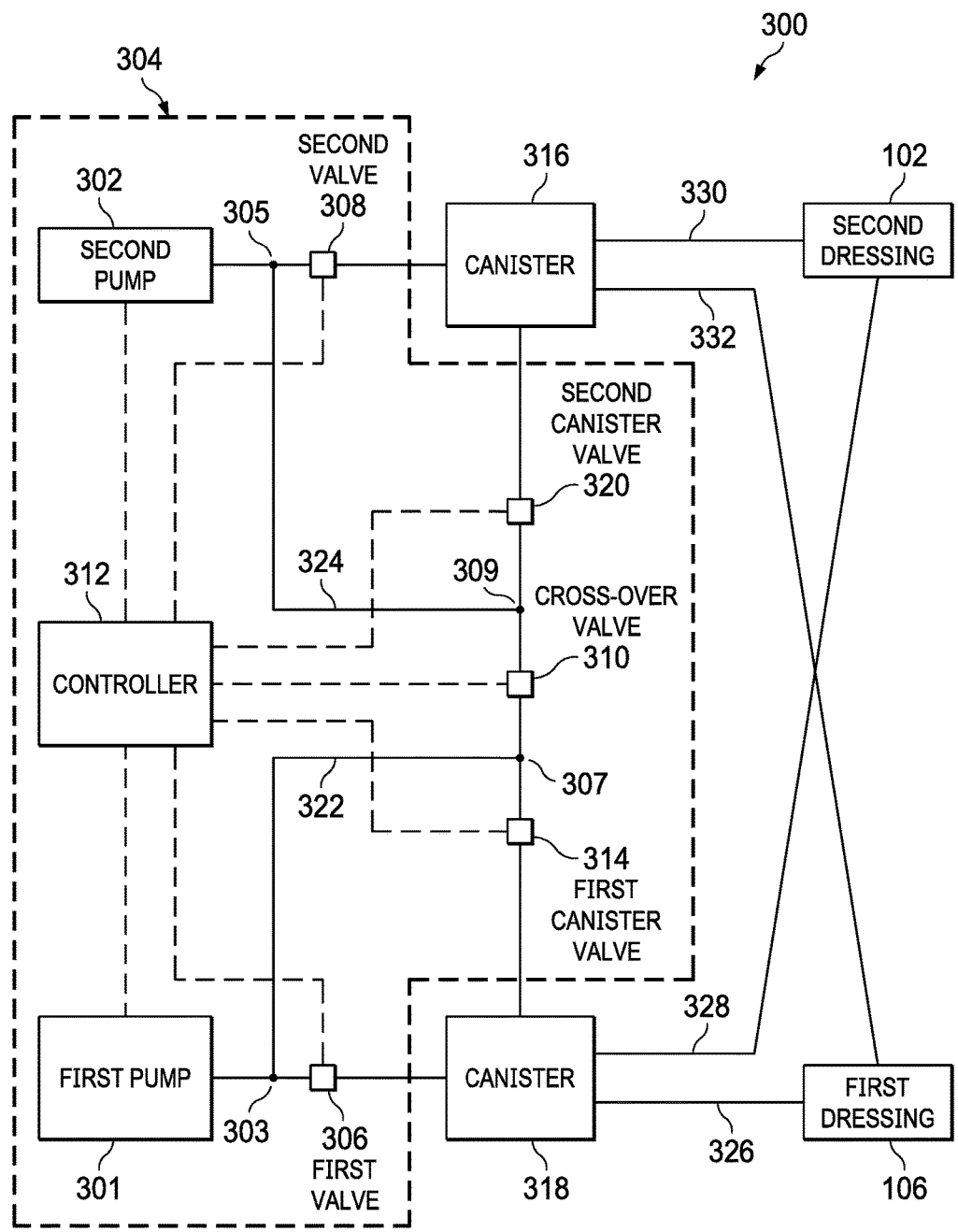
FIG. 3 is a schematic diagram illustrating additional details that may be associated with another example embodiment of the negative-pressure therapy system of FIG. 1.

FIG. 3 is a schematic view of a negative-pressure therapy system 300, illustrating details that may be associated with another embodiment, comprising a negative-pressure source 304 that includes a first pump 301 and a second pump 302. The negative-pressure therapy system 300 may include the dressing 102 and the dressing 106. The negative-pressure therapy system 300 may also include a canister 316 and a canister 318. The canister 316 and the canister 318 may be similar to and operate as described above with respect to the canister 116 and the canister 118.

The first pump 301 and the second pump 302 may be similar to and operate as described above with respect to the first pump 201 and the second pump 202. In some embodiments, the first pump 301 and the second pump 302 may have a same capacity. For example, both the first pump 301 and the second pump 302 may have a free-air-flow capacity between about 7 lpm and about 9 lpm. In other embodiments, the first pump 301 and the second pump 302 may have different capacities. For example, the first pump 301 may have a free-air-flow capacity between about 7 lpm and about 9 lpm, and the second pump 302 may have a free-air-flow capacity between about 0.3 lpm and about 0.7 lpm. The negative-pressure source 304 may also include a first valve 306, a second valve 308, and a controller 312. The first valve 306, the second valve 308, and the controller 312 may be similar to and operate as described above with respect to the first valve 206, the second valve 208, and the controller 212. The first valve 306 may be fluidly coupled between the first pump 301 and the canister 318. Similarly, the second valve 308 may be fluidly coupled between the second pump 302 and the canister 316. The controller 312 may be communicatively coupled to the first pump 301, the second pump 302, the first valve 306, and the second valve 308 for operation of the communicatively coupled devices.

The negative-pressure source 304 may also include a cross-over valve 310, a first canister valve 314, and a second canister valve 320. The cross-over valve 310, the first canister valve 314, and the second canister valve 320 may be valves similar to those described above. The cross-over valve 310 may have a first port fluidly coupled to the canister 316 and a second port fluidly coupled to the canister 318. The first canister valve 314 may be fluidly coupled between the cross-over valve 310 and the canister 318. The second canister valve 320 may be fluidly coupled between the cross-over valve 310 and the canister 316. In some embodiments, the cross-over valve 310, the first canister valve 314, and the second canister valve 320 may be communicatively coupled to the controller 312.

In some embodiments, the negative-pressure source 304 may include a first bypass tube 322 having a first end fluidly coupled by a tee-fitting 303 between an outlet of the first pump 301 and the first valve 306. The first bypass tube 322 may have a second end fluidly coupled by a tee-fitting 307 between the cross-over valve 310 and the first canister valve 314. The first bypass tube 322 may provide a fluid path that bypasses the first valve 306. In some embodiments, the negative-pressure source 304 may also include a second bypass tube 324. The second bypass tube 324 may have a first end fluidly coupled by a tee-fitting 305 between an outlet of the second pump 302 and the second valve 308. The second bypass tube 324 may have a second end fluidly coupled by a tee-fitting 309 between the cross-over valve 310 and the second canister valve 320. The second bypass tube 324 may provide a fluid path that bypasses the second valve 308.

In some embodiments, the negative-pressure therapy system 300 may include a tube 326 fluidly coupled between the dressing 106 and the canister 318. The negative-pressure therapy system 300 may also include a tube 328 fluidly coupling the canister 318 to the dressing 102. Similarly, the negative-pressure therapy system 300 may include a tube 330 fluidly coupling the canister 316 to the dressing 102 and a tube 332 fluidly coupling to the canister 316 to the dressing 106. In some embodiments, negative pressure provided to the canister 318 may be fluidly communicated to the dressing 106 through the tube 326 and to the dressing 102 through the tube 328. Similarly, negative pressure provided to the canister 316 may be fluidly communicated to the dressing 102 through the tube 330 and to the dressing 106 through the tube 332.

In some embodiments, the cross-over valve 310 may be closed during operation of the first pump 301 and the second pump 302. If the cross-over valve 310 is closed, at least one of the first valve 306 or the first canister valve 314 may be open while the first pump 301 is operating. In this configuration, the first pump 301 may provide negative pressure to the canister 318 through one or both of the first valve 306 or the first canister valve 314. Similarly, at least one of the second valve 308 and the second canister valve 320 may be open while the second pump 302 is operating. In this configuration, the second pump 302 may provide negative pressure to the canister 316 through one or both of the second valve 308 or the second canister valve 320.

In some embodiments, the cross-over valve 310 may be open during operation of the first pump 301 and the second pump 302. If the cross-over valve 310 is open, the negative-pressure therapy system 300 may provide therapy to the dressing 102 and the dressing 106 through the canister 318, the canister 316, or both the canister 318 and the canister 316. For example, if the cross-over valve 310 is open and either the first valve 306 or the first canister valve 314 is open, the first pump 301 may provide negative-pressure to the canister 318. If either the second valve 308 or the second canister valve 320 is open, the first pump 301 may also provide negative pressure to the canister 316. If the first valve 306 and the first canister valve 314 are closed and either the second valve 308 or the second canister valve 320 is open, the first pump 301 may provide negative pressure to the canister 316 and not to the canister 318.

Similarly, if the cross-over valve 310 is open and either the second valve 308 or the second canister valve 320 is open, the second pump 302 may provide negative pressure to the canister 316. If either of the first valve 306 or the first canister valve 314 is open, the second pump 302 may also provide negative pressure to the canister 318. If the second valve 308 and the second canister valve 320 are closed, the second pump 302 may provide negative pressure to the canister 318 and not to the canister 316.

In some embodiments, the negative-pressure therapy system 300 may provide multiple fluid paths through which negative pressure may be provided to the dressing 102 and the dressing 106. For example, the negative-pressure source 304 may provide negative pressure to the canister 318 and the canister 316, only the canister 316, or only the canister 318 by operating the valves as described above. In this manner, the negative-pressure source 304 may select the path of least resistance to the provision of negative pressure. For example, if the canister 318 becomes full or the fluid path through the canister 318 becomes clogged or impassable, the negative-pressure source 304 may operate to provide negative pressure to the dressing 102 and the dressing 106 through the canister 316. Similarly, if the canister 316 becomes full or the fluid path through the canister 316 becomes clogged or impassable, the negative-pressure source 301 may operate to provide negative pressure to the dressing 102 and the dressing 106 through the canister 318.

Figure 4:
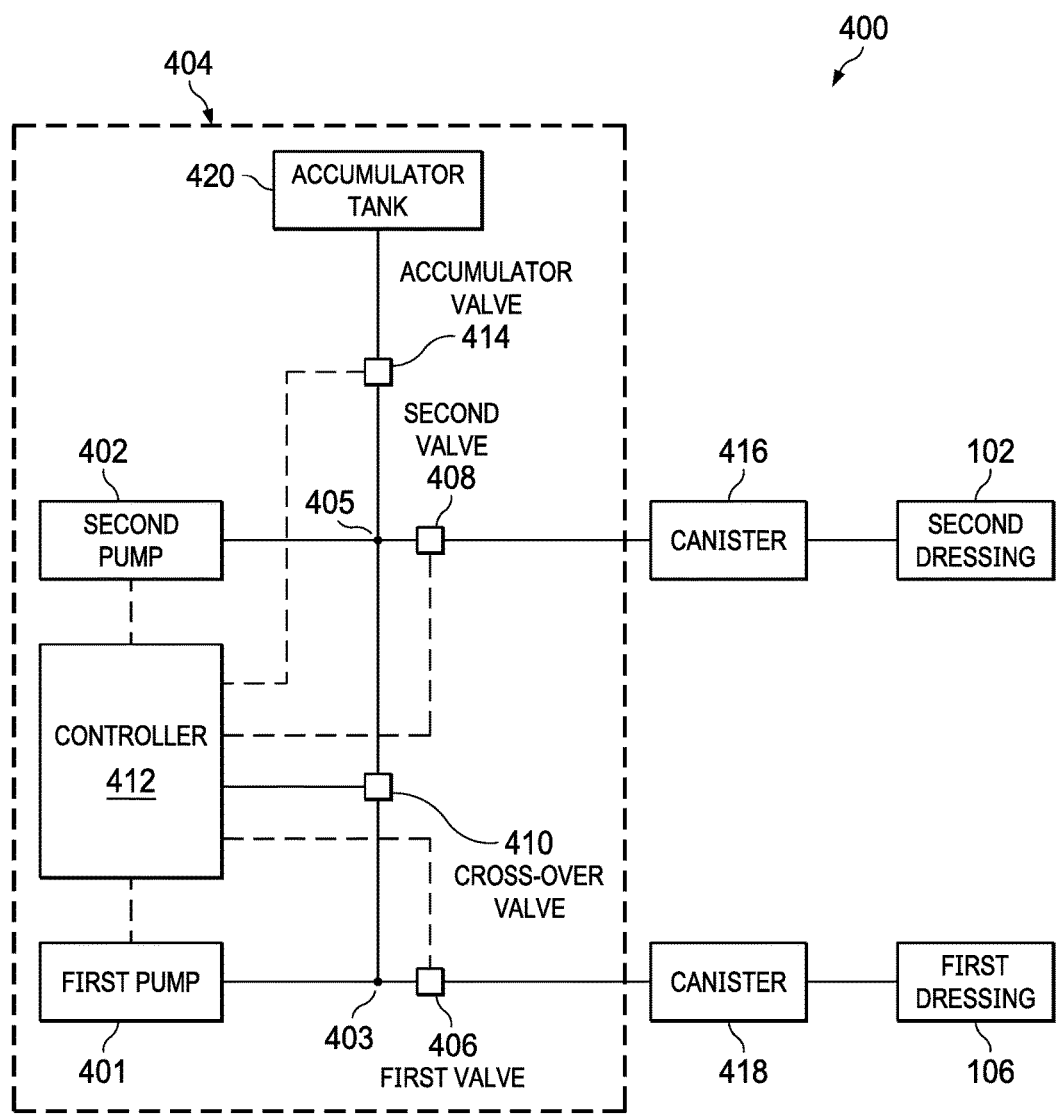
FIG. 4 is a schematic diagram illustrating additional details that may be associated with another example embodiment of the negative-pressure therapy system of FIG. 1.

FIG. 4 is a schematic view of a negative-pressure therapy system 400, illustrating details that may be associated with another embodiment, comprising a negative-pressure source 404 that includes a first pump 401 and a second pump 402. The negative-pressure therapy system 400 may include the dressing 102 and the dressing 106. The negative-pressure therapy system 400 may also include a canister 416 and a canister 418. The canister 416 and the canister 418 may be similar to and operate as described above with respect to the canister 116 and the canister 118.

The first pump 401 and the second pump 402 may be similar to and operate as described above with respect to the first pump 201 and the second pump 202. The negative-pressure source 404 may also include a first valve 406, a second valve 408, and a controller 412. The first valve 406, the second valve 408, and the controller 412 may be similar to and operate as described above with respect to the first valve 206, the second valve 208, and the controller 212. The first valve 406 may be fluidly coupled between the first pump 401 and the canister 418. Similarly, the second valve 408 may be fluidly coupled between the second pump 402 and the canister 416. The controller 412 may be communicatively coupled to the first pump 401, the second pump 402, the first valve 406, and the second valve 408 for operation of the communicatively coupled devices.

The negative-pressure source 404 may also include a cross-over valve 410. The cross-over valve 410 may be similar to and operate as described above with respect to the cross-over valve 210. The cross-over valve 410 may have a first port fluidly coupled by a tee-fitting 403 to the first pump 401 and the first valve 406 and a second port fluidly coupled by a cross-fitting 405 to the second pump 402 and the second valve 408. The controller 412 may be communicatively coupled to the cross-over valve 410 and configured to operate the cross-over valve 410.

The negative-pressure source 404 may also include an accumulator tank 420 and an accumulator valve 414. The accumulator tank 420 may be fluidly coupled between the second pump 402 and the second valve 408 and between the first pump 401 and the first valve 406 through the cross-over valve 410. The accumulator valve 414 may be fluidly coupled between the accumulator tank 420 and the remainder of the negative-pressure source 404. In some embodiments, the accumulator valve 414 may be a valve that is similar to the first valve 402, the second valve 408, and the cross-over valve 410. An accumulator tank, such as the accumulator tank 420, may be a reservoir or pressure vessel capable of storing negative pressure. In some embodiments, the accumulator tank 420 may having a volume between about 100 ml and about 1 liter. In other embodiments, the accumulator tank 420 may have a volume that is greater than about 1 liter. The controller 412 may be communicatively coupled to the accumulator valve 414 and the accumulator tank 420.

Generally, the negative-pressure source 404 may operate as described above with respect to the negative-pressure source 204. In some embodiments, the negative-pressure source 404 my store negative-pressure in the accumulator tank 420. For example, the negative-pressure source 404 may operate as described above to provide negative-pressure to the dressing 102 and the dressing 106. If the dressing 102 and the dressing 106 are at the therapy pressure, the controller 412 may close the first valve 406 and the second valve 408 and open the cross-over valve 410 and the accumulator valve 414. The controller 412 may operate one or both of the first pump 401 and the second pump 402 to provide negative pressure to the accumulator tank 420. If the accumulator tank 420 reaches capacity, the controller 412 may close the accumulator valve 414, storing the negative pressure in the accumulator tank 410. If additional negative pressure is needed in the dressing 102 or the dressing 106, the controller 412 may open the accumulator valve 414 and one or more of the first valve 406, the cross-over valve 410 and the second valve 408 to provide negative pressure to the one or both of the dressing 102 and the dressing 106. In this manner, the negative-pressure source 404 may provide supplemental negative pressure during negative-pressure therapy without requiring additional operation of the first pump 401 or the second pump 402.

In some embodiments, a negative pressure source may have three pumps. One pump of the three pumps may be a larger pump for quickly drawing-down one or more dressings. Two of the pumps may be smaller pumps to maintain pressure at the one or more dressings. In some embodiments, components from the negative-pressure therapy system 100 of FIG. 1, the negative-pressure therapy system 200 of FIG. 2, the negative-pressure therapy system 300 of FIG. 3, and the negative-pressure therapy system 400 of FIG. 4 may be combined. In some embodiments, the negative-pressure therapy system 100, the negative-pressure therapy system 200, the negative-pressure therapy system 300, and the negative-pressure therapy system 400 may include more than two pumps and additional valves so that they systems may be expanded. In some embodiments, the negative-pressure therapy system 100, the negative-pressure therapy system 200, the negative-pressure therapy system 300, and the negative-pressure therapy system 400 may be fluidly coupled to more than two tissue sites.

Figure 5:
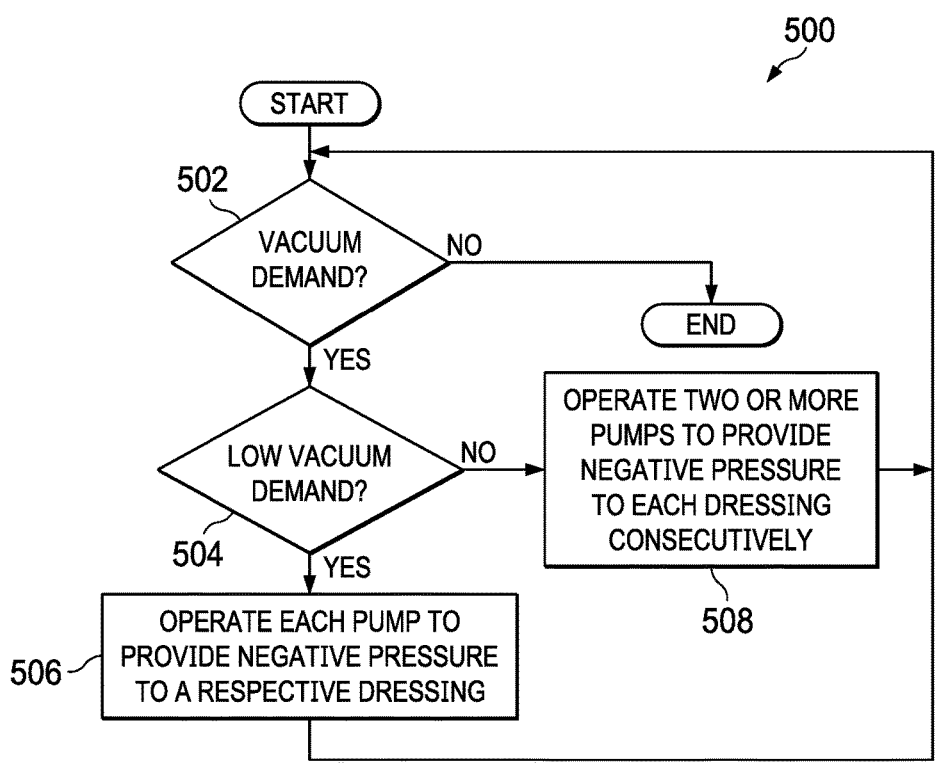
FIG. 5 is a flow chart depicting logical operational steps of a method for providing reduced-pressure therapy in accordance with some embodiments.

FIG. 5 illustrates a flow chart 500 of logical operations in a process that can be implemented in some embodiments of the negative-pressure therapy system 200 of FIG. 2, the negative-pressure therapy system 300 of FIG. 3, or the negative-pressure therapy system 400 of FIG. 4 during negative-pressure therapy. For example, the operations may be implemented by a controller configured to execute the operations. At block 502, the process determines if there is a vacuum demand. For example, the controller 212 may determine if there is a vacuum demand from the dressing 102, the dressing 106, the canister 116, or the canister 118 with one or more sensors communicatively coupled to the controller 212. If there is no vacuum demand (NO), the process ends.

If there is a vacuum demand at block 502 (YES), the process continues to block 504, where the process determines if the vacuum demand is a low vacuum demand. For example, once the dressing 102 and the dressing 106 reach the therapy pressure, the controller 212 may determine if the negative pressure required to provide or maintain negative-pressure therapy to the dressing 102 and the dressing 106 is less than about 0.5 lpm. If the vacuum demand is low at block 504 (YES), the process continues to block 506, where the process may operate each pump of the two or more pumps to independently provide negative pressure to a respective dressing and returns to block 502 to determine if there is a vacuum demand. For example, the controller 212 may open the first valve 206 and the second valve 208, close the cross-over valve 210, and operate the first pump 201 to provide negative pressure to the canister 118 and the dressing 106 and the second pump 202 to provide negative pressure to the canister 116 and the dressing 102. The process continues to block 502, where the process determines if there is a vacuum demand.

If there is a high vacuum demand at block 504 (NO), the process continues to block 508, where the process may operate each pump of the two or more pumps to provide negative pressure to each dressing consecutively. For example, if the negative-pressure demand is greater than about 0.5 lpm, the process controller 212 closes the second valve 208, opens the first valve 206 and the cross-over valve 210, and operates the first pump 201 and the second pump 202 to provide negative pressure to the canister 118 and the dressing 106. If the canister 118 and the dressing 106 do not require additional negative pressure, the controller 212 closes the first valve 206, opens the second valve 208 and the cross-over valve 210, and operates the first pump 201 and the second pump 202 to provide negative pressure to the canister 116 and the dressing 102. The process continues to block 502, where the process determines if there is a vacuum demand.

Figure 6:
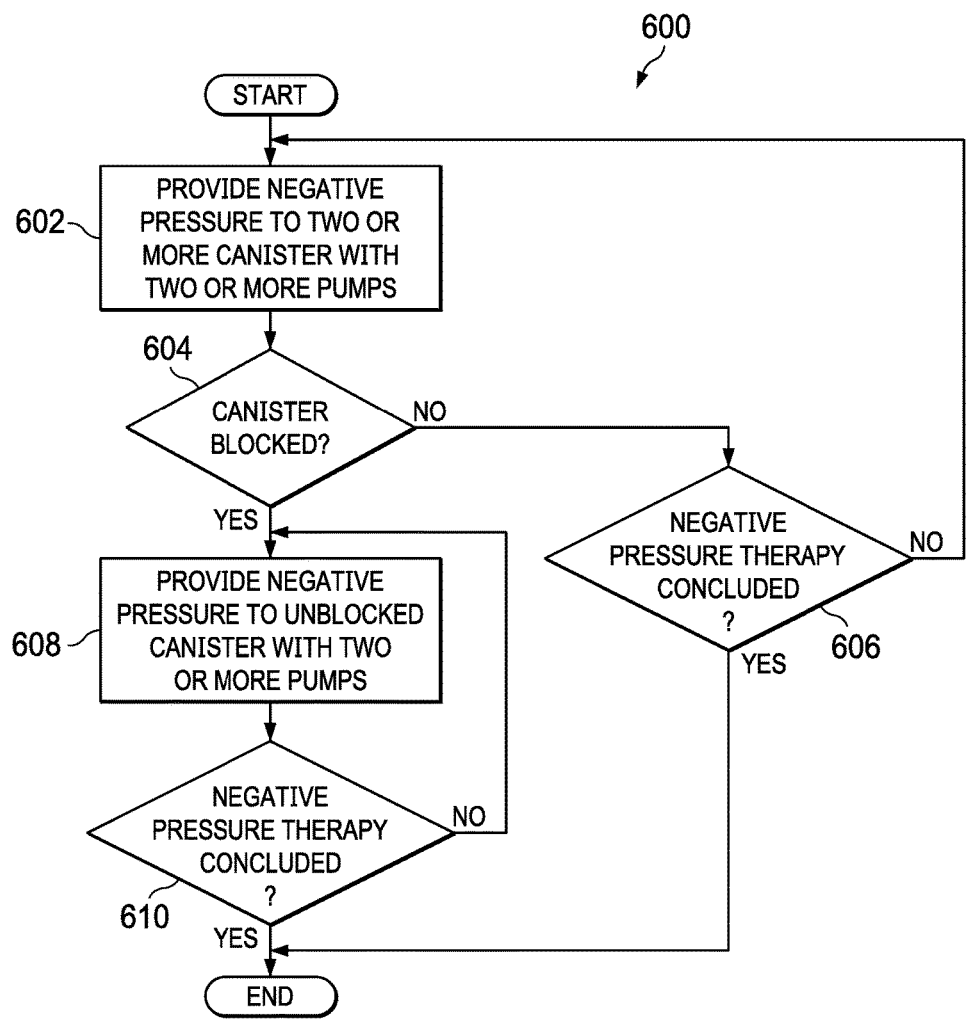
FIG. 6 is a flow chart depicting logical operational steps of another method for providing reduced-pressure therapy in accordance with some embodiments.

FIG. 6 illustrates a flow chart 600 of logical operations in a process that can be implemented in some embodiments of the negative-pressure therapy system 200 of FIG. 2, the negative-pressure therapy system 300 of FIG. 3, or the negative-pressure therapy system 400 of FIG. 4 during negative-pressure therapy. For example, the operations may be implemented by a controller configured to execute the operations. At block 602, the process provides negative pressure to two or more canister with two or more pumps. For example, the controller 312 closes the cross-over valve 310, opens the first valve 306 and the second valve 308, and operates the first pump 301 and the second pump 302 to provide negative pressure to the canister 318 and the canister 316, respectively.

The process continues at block 604, where the process determines if one of the canisters is blocked. For example, the controller 312 may monitor one or more pressure sensors or flow sensors to determine if there is fluid flow through the canister 318 or the canister 316. If no canister is blocked at block 604 (NO), the process continues to block 606, where the process determines if negative-pressure therapy is concluded. For example, the controller 312 determines if negative-pressure therapy is concluded. If negative-pressure therapy has not concluded (NO), the process continues to block 602, where the process continues. If negative-pressure therapy has concluded (YES), the process ends.

If a canister is blocked at block 604 (YES), the process continues to block 608, where the process provides negative pressure to the unblocked canisters. For example, if the canister 318 is blocked, the controller 312 may close the first valve 306 and the first canister valve 314, open the cross-over valve 310, the first canister valve 320, and the second valve 308, and operate the first pump 301 and the second pump 302 to provide negative pressure to the canister 316. Negative pressure may be communicated to the dressing 102 and the dressing 106 through the tube 330 and the tube 332, respectively. The process continues to block 610 where the process determines if negative-pressure therapy is concluded. For example, the controller 312 determines if negative-pressure therapy is concluded. If negative-pressure therapy has not concluded (NO), the process continues to block 608, where the process continues. If negative-pressure therapy has concluded (YES), the process ends.

Figure 7:
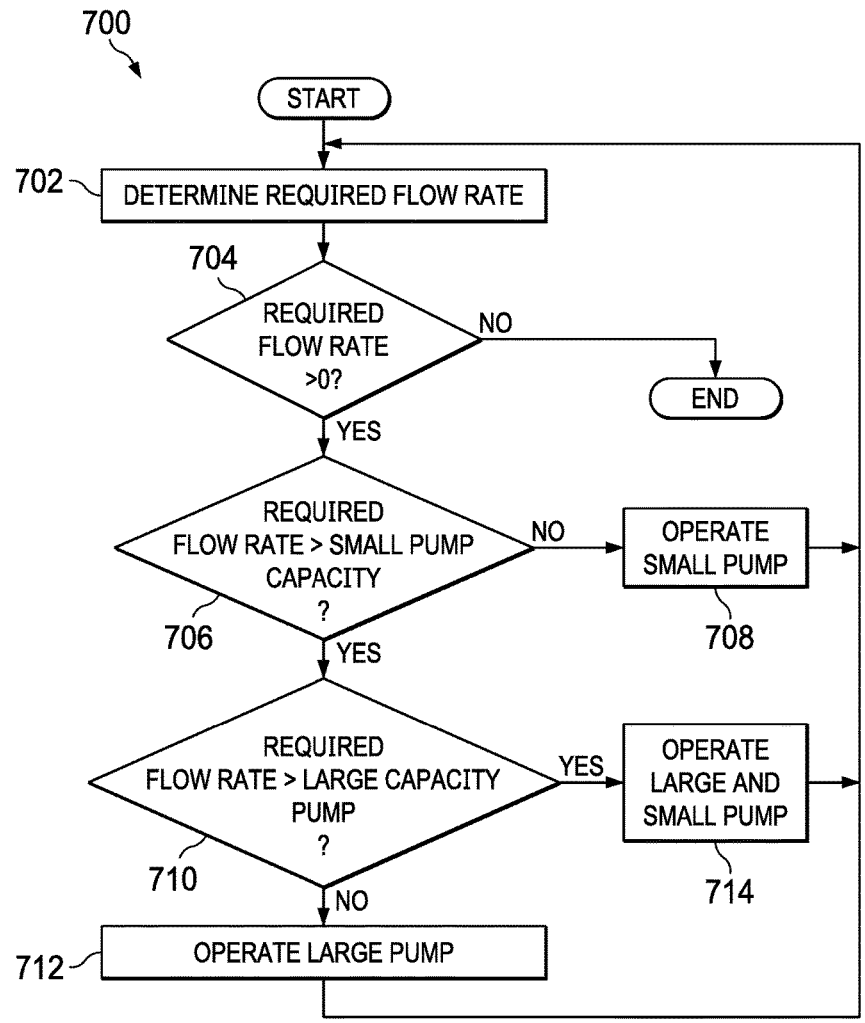
FIG. 7 is a flow chart depicting logical operational steps of another method for providing reduced-pressure therapy in accordance with some embodiments.

FIG. 7 illustrates a flow chart 700 of logical operations in a process that can be implemented in some embodiments of the negative-pressure therapy system 200 of FIG. 2, the negative-pressure therapy system 300 of FIG. 3, or the negative-pressure therapy system 400 of FIG. 4 during negative-pressure therapy. For example, the operations may be implemented by a controller configured to execute the operations with a negative-pressure therapy system having a higher capacity pump and a lower capacity pump. With respect to the flow chart of FIG. 7, the first pump 201 of the negative-pressure system 100 of FIG. 2 may be a higher capacity pump, and the second pump 202 may be a lower capacity pump.

At block 702, the process determines a required flow rate, which may be the flow rate of negative pressure required to provide the therapy pressure. For example, the controller 212 may determine the flow rate of negative pressure required to provide the therapy pressure to the dressing 102 and the dressing 106. At block 704, the process determines if the required flow rate is greater than 0 lpm. If the required flow rate is not greater than 0 lpm (NO), the process ends. If the required flow rate is greater than 0 lpm (YES), the process continues to block 706.

At block 706, the process determines if the required flow rate is greater than a smaller capacity pump. For example, the controller 212 determines if the required flow rate is greater than the capacity of the second pump 202. If the required flow rate is not greater than the capacity of the smaller capacity pump (NO), the process continues to block 708, where the process operates the smaller capacity pump to provide negative-pressure therapy. For example, the controller 212 opens the first valve 206, the cross-over valve 210, and the second valve 208 and operates the second pump 202 to provide negative pressure to the canister 118 and the canister 116. The process continues to block 702 where the process determines the required flow rate.

If the required flow rate is greater than the capacity of the smaller capacity pump at block 706 (YES), the process continues to block 710, where the process determines if the required flow rate is greater than the capacity of the larger capacity pump. If the required flow rate is not greater than the capacity of the larger capacity pump (NO), the process continues to block 712, where the process operates the larger capacity pump. For example, the controller 212 opens the first valve 206, the cross-over valve 210, and the second valve 208 and operates the first pump 201 to provide negative pressure to the canister 118 and the canister 116. If the required flow rate is greater than the capacity of the larger capacity pump at block 710 (YES), the process continues to block 714, where the process operates both the smaller capacity pump and the larger capacity pump to provide negative-pressure therapy. For example, the controller 212 opens the first valve 206, the cross-over valve 210, and the second valve 208 and operates the first pump 201 and the second pump 202 to provide negative pressure to the canister 118 an the canister 116. The process continues to block 702 where the process determines the required flow rate.

The systems, apparatuses, and methods described herein may provide significant advantages. For example, the system may provide redundancy if a pump performance issue is detected. For example, if one pump is operating outside of the desired parameters, the other pump may be used to supplement or replace the improperly operating pump. The system may also provide a multi-channel therapy system by opening different fluid pathways, as needed, to make up for dressing leaks or system blockages. The system may also provide pump optimization to reduce power consumption. The system can include a higher capacity pump to use for quick drawdown of any fluid channel and reduce caregiver time. Once a dressing is drawn down and reasonably sealed, a lower capacity pump can be used to make up for typical dressing leak rates. A lower capacity pump can be more readily optimized to reduce power consumption and extend battery life of the system. The system can also provide a higher capacity pump to use during leak-finding. The system may provide a higher capacity pump in combination with one or more lower capacity pumps that can reduce the overall weight of the portable system by both reducing the total weight of the pumps and by reducing the size and weight of the battery required to operate the pumps for a specified time.

The system may also provide acoustic benefits. By combining a higher capacity pump and one or more smaller capacity pumps, the noise during operation of the device may be tailored to provide louder operation during drawdown which is typically short-term and thus acceptable. The lower capacity pumps generate less noise and may be more acceptable for longer-term use, such as while providing therapy while the patient sleeps. The system may also be scalable to include additional pumps that may be incorporated with the addition of more valves.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A negative-pressure therapy system, comprising:
    a first dressing adapted to be positioned adjacent a first tissue site;
    a second dressing adapted to be positioned adjacent a second tissue site;
    a negative-pressure source comprising:
        a first pump having an outlet and adapted to be fluidly coupled to the first dressing,
        a second pump having an outlet and adapted to be fluidly coupled to the second dressing,
        a first valve having an outlet fluidly coupled to the first dressing and an inlet fluidly coupled to the outlet of the first pump and adapted to selectively permit fluid communication to the first dressing,
        a second valve having an outlet fluidly coupled to the second dressing and an inlet fluidly coupled to the outlet of the second pump and adapted to selectively permit fluid communication to the second dressing,
        a cross-over valve having a first port fluidly coupled to the outlet of the first pump and the inlet of the first valve and a second port fluidly coupled to the outlet of the second pump and the inlet of the second valve, the cross-over valve adapted to selectively permit fluid communication between the outlet of the first pump and the inlet of the second valve and/or the outlet of the second pump and the inlet of the first valve; and
    a controller communicatively coupled to the first pump, the second pump, the first valve, the second valve, and the cross-over valve for selectively operating the first pump, the second pump, the first valve, the second valve, and the cross-over valve.

2. The negative-pressure therapy system of claim 1, further comprising:
    an accumulator valve having an inlet fluidly coupled to the outlet of the first pump, the outlet of the second pump, the inlet of the first valve, the inlet of the second valve, and at least one of the first port and the second port of the cross-over valve; and an accumulator tank fluidly coupled to an outlet the accumulator valve;

wherein the controller is communicatively coupled to the accumulator valve for selectively operating the accumulator valve.

3. The negative-pressure therapy system of claim 1, wherein:

the first dressing is fluidly coupled to the outlet of the second valve;

the second dressing is fluidly coupled to the outlet of the first valve; and the negative-pressure source further comprises:
a first canister valve having an inlet fluidly coupled to the first port of the cross-over valve and an outlet fluidly coupled to the outlet of the first valve, the first dressing, and the second dressing, the first canister valve adapted to selectively permit fluid communication with the first dressing, and a second canister valve having an inlet fluidly coupled to the second port of the cross-over valve and an outlet fluidly coupled to the outlet of the second valve, the first dressing, and the second dressing, the second canister valve adapted to selectively permit fluid communication with the second dressing.

4. The negative-pressure therapy system of claim 3, further comprising:

a first canister fluidly coupled to the first dressing, the second dressing, the outlet of the first valve, and the outlet of the first canister valve;

a second canister fluidly coupled to the second dressing, the first dressing, the outlet of the second valve, and the outlet of the second canister valve.

5. The negative-pressure therapy system of claim 4, wherein the controller is configured to operate the first valve, the second valve, the first canister valve, the second canister valve, and the cross-over valve to provide negative-pressure to a first canister, a second canister, or both the first canister and the second canister.

6. The negative-pressure therapy system of claim 1, wherein the first dressing further comprises:

a tissue interface adapted to be positioned adjacent to the first tissue site; and a first sealing member adapted to cover the tissue interface and seal to the first tissue site.

7. The negative-pressure therapy system of claim 6, wherein the first tissue interface is a manifold.

8. The negative-pressure therapy system of claim 1, wherein the first pump has a greater capacity than the second pump.

9. The negative-pressure therapy system of claim 1, wherein:

the first pump has a capacity between about 7 liters per minute (lpm) and about 9 lpm; and the second pump has a capacity between about 0.3 lpm and about 0.7 lpm.

10. The negative-pressure therapy system of claim 1, wherein the first pump has a capacity between about 7 lpm and about 9 lpm.

11. The negative-pressure therapy system of claim 1, wherein the second pump has a capacity between about 0.3 lpm and about 0.7 lpm.

12. A negative-pressure source, comprising:

a first pump;

a second pump;

a first valve having an inlet fluidly coupled to an outlet of the first pump;

a second valve having an inlet fluidly coupled to an outlet of the second pump;

a cross-over valve having a first port fluidly coupled the outlet of the first pump and the inlet of the first valve, and a second port fluidly coupled to the outlet of the second pump and the inlet of the second valve; and a controller communicatively coupled to the first pump, the second pump, the first valve, the second valve, and the cross-over valve for operation of the first pump, the second pump, the first valve, the second valve, and the cross-over valve.

13. The negative-pressure source of claim 12, further comprising:

an accumulator valve having an inlet fluidly coupled to the outlet of the first pump, the outlet of the second pump, the inlet of the first valve, the inlet of the second valve, and at least one of the first port and the second port of the cross-over valve; and an accumulator tank fluidly coupled to an outlet the accumulator valve;

wherein the controller is communicatively coupled to the accumulator valve for selectively operating the accumulator valve.

14. The negative-pressure source of claim 12, further comprising:

a first canister valve having an inlet fluidly coupled to the first port of the cross-over valve and an outlet fluidly coupled to the outlet of the first valve, a first dressing, and a second dressing; and a second canister valve having an inlet fluidly coupled to the second port of the cross-over valve and an outlet fluidly coupled to the outlet of the second valve, the first dressing, and the second dressing.

15. The negative-pressure source of claim 14, wherein the controller is configured to operate the first valve, the second valve, the first canister valve, the second canister valve, and the cross-over valve to provide negative-pressure to a first canister, a second canister, and both the first canister and the second canister.

16. The negative-pressure source of claim 12, wherein the first pump has a greater capacity than the second pump.

17. The negative-pressure source of claim 12, wherein:

the first pump has a capacity between about 7 liters per minute (lpm) and about 9 lpm; and the second pump has a capacity between about 0.3 lpm and about 0.7 lpm.

18. The negative-pressure source of claim 12, wherein the first pump has a capacity between about 7 lpm and about 9 lpm.

19. The negative-pressure source of claim 12, wherein the second pump has a capacity between about 0.3 lpm and about 0.7 lpm.

* * * * *